United States Patent
Widick (10) Patent No.: US 10,501,715 B1
(45) Date of Patent: Dec. 10, 2019

(54) SYSTEM FOR THE FORMATION OF FIBRIN FOAM

(71) Applicant: Mark H. Widick, Boca Raton, FL (US)

(72) Inventor: Mark H. Widick, Boca Raton, FL (US)

( * ) Notice: Subject to any disclaimer, the term of this patent is extended or adjusted under 35 U.S.C. 154(b) by 127 days.

(21) Appl. No.: 15/262,157

(22) Filed: Sep. 12, 2016

Related U.S. Application Data (60) Provisional application No. 62/217,460, filed on Sep. 11, 2015.

(51) Int. Cl.
| | |
|---|---|
| *B01L 1/00* | (2006.01) |
| *B01L 3/00* | (2006.01) |
| *C12M 1/26* | (2006.01) |
| *C12P 21/06* | (2006.01) |
| *C12M 1/40* | (2006.01) |
| *C12M 1/12* | (2006.01) |
| *C12M 1/00* | (2006.01) |
| *C12M 3/00* | (2006.01) |

(52) U.S. Cl.
CPC ............ *C12M 33/10* (2013.01); *C12M 21/18* (2013.01); *C12M 23/34* (2013.01); *C12M 23/42* (2013.01); *C12M 25/18* (2013.01); *C12M 29/14* (2013.01); *C12M 47/10* (2013.01); *C12P 21/06* (2013.01)

(58) Field of Classification Search
CPC . C12M 45/05; C12M 47/02; B01L 3/502753; B01L 2400/0409
See application file for complete search history.

(56) References Cited

U.S. PATENT DOCUMENTS

| | | | |
|---|---|---|---|
| 2,492,458 | A | 12/1949 | Bering, Jr. |
| 3,523,807 | A | 8/1970 | Gerendas |
| 3,723,244 | A | 3/1973 | Breillatt, Jr. |
| 4,548,739 | A | 10/1985 | Muller et al. |
| 5,030,215 | A | 7/1991 | Morse et al. |
| 5,180,391 | A | 1/1993 | Beoni |
| 5,510,077 | A | 4/1996 | Dinh et al. |
| 5,585,007 | A | 12/1996 | Antanavich et al. |
| 5,603,845 | A | 2/1997 | Holm |
| 5,707,331 | A | 1/1998 | Wells et al. |
| 5,733,446 | A | 3/1998 | Holm |
| 5,733,545 | A | 3/1998 | Hood, III |
| 5,741,428 | A | 4/1998 | Holm |
| 5,763,410 | A | 6/1998 | Edwardson et al. |
| 5,788,662 | A | 8/1998 | Antanavich et al. |

(Continued)

*Primary Examiner* — Nathan A Bowers
(74) *Attorney, Agent, or Firm* — Malloy & Malloy, PA (57) ABSTRACT

A system for forming fibrin foam, preferably utilizing a single container, comprising a cartridge structured to be rotationally driven and including a primary chamber disposed and structured to receive a blood sample therein. The cartridge further includes reaction and cell chambers independently disposed in fluid communication with said primary chamber. The blood sample is separated into a plasma segment and a packed cell segment when subjected to sufficient centrifugation concurrent to the driven rotation of the cartridge. Concurrent to the centrifugation of the canister, the plasma segment is directed from said primary chamber into said reaction chamber and the packed cell segment is directed from an interior of said primary chamber to an exterior thereof, such as into the cell chamber. The reaction chamber includes sufficient quantities of gas and reactant composition to facilitate formation of fibrin foam therein concurrent to centrifugation.

15 Claims, 6 Drawing Sheets

(56) References Cited

U.S. PATENT DOCUMENTS

| | | | |
|---|---|---|---|
| 5,795,489 A | | 8/1998 | Holm |
| 6,063,297 A | | 5/2000 | Antanavich et al. |
| 6,063,589 A | * | 5/2000 | Kellogg .............. B01F 13/0059 366/DIG. 3 |
| 6,143,247 A | * | 11/2000 | Sheppard, Jr. ...... B01F 13/0059 210/109 |
| 6,368,298 B1 | | 4/2002 | Beretta et al. |
| 6,548,729 B1 | | 4/2003 | Seelich et al. |
| 6,965,014 B1 | | 11/2005 | Delmonte et al. |
| 8,119,013 B2 | | 2/2012 | Leach et al. |
| 8,226,942 B2 | | 7/2012 | Charier et al. |
| 8,512,741 B2 | | 8/2013 | Delmonte |
| 8,641,661 B2 | | 2/2014 | Delmonte |
| 8,753,670 B2 | | 6/2014 | Delmonte |
| 8,846,105 B2 | | 9/2014 | Koopman et al. |
| 2011/0251041 A1 | * | 10/2011 | Chavarria ........... A61M 1/3693 494/4 |
| 2015/0314289 A1 | * | 11/2015 | Kellogg ............... G01N 33/491 435/309.1 |

* cited by examiner

SYSTEM FOR THE FORMATION OF FIBRIN FOAM

CLAIM OF PRIORITY

This Non-Provisional patent application hereby makes a claim of priority to an earlier filed and currently U.S. provisional patent application having Ser. No. 62/217,460 and a filing date of Sep. 11, 2015, which is incorporated herewith in its entirety.

BACKGROUND OF THE INVENTION

Field of the Invention

The present invention is directed to a system including structural and operative features for the formation of fibrin foam, preferably within a single container/canister structured to be centrifuged by or as part of a rotational drive assembly. Centrifugation of the canister results in separation of a blood sample into at least a plasma segment and a packed cell segment, wherein the plasma segment is directed into a reaction chamber of in the canister which contains sufficient quantities of gas and reactant composition to facilitate the formation of fibrin foam or corresponding fibrin products, concurrent to centrifugation.

Description of the Related Art

Numerous procedures have been attempted in an effort to create and/or form tissue sealants, adhesives, films, foam matrices, etc. applicable for use in surgical procedures. Known tissue supplements include natural fibrin glues, sealants, etc. made from blood components. Surgical fibrin components may be made up from human fibrinogen activated by a thrombin-like enzyme such as thrombin itself or any other material with a similar activity. Such fibrin components have been shown to be superior to similar synthetic components for use in traditional surgery in many different situations. Accordingly, it is recognized that fibrin glue, sealants, foam, etc. and like fibrin products have many advantages over related or corresponding synthetic components for surgical use.

Currently, such fibrin components are made by isolating a concentrate of human fibrinogen, such as by cryoprecipitation, and combining it before use with a bovine or human thrombin, as generally set forth above. The thrombin enzyme converts the fibrinogen to fibrin which rapidly gels into a foam, film or like consistently textured matrix. Similarly, the most common method of application of fibrin components include the mixing of concentrated fibrinogen from pooled human blood with a thrombin enzyme and calcium immediately before use.

However, few if any of known or existing prior art methods or procedures are readily adaptable for the convenient and efficient use of an autologous plasma fraction which can be prepared quickly during a surgical procedure. As is commonly recognized, autologous blood products are superior for safety and biocompatibility reasons. More specifically, known and existing prior art procedures for the formation of a fibrin tissue supplements utilizing the preparation of a fibrinogen containing fraction for this purpose are time-consuming and frequently too complex to be completed in a short enough time to be accomplished during the surgical procedure. Also, known prior art procedures frequently involve the use of complicated, specialized equipment, which also presents problems with the efficient creation of fibrin foam or like fibrin products.

To overcome such disadvantages and problems attempts have been made to prepare fibrin compositions in advance. However this imposes the necessity or requirement of utilizing additional procedures for identification and retrieval of the samples matched with a given patient. In turn there exists an opportunity for error besides inconvenience, at least to the extent of requiring additional time, appointments, etc. of both the patient and corresponding medical personnel. As should be apparent, such preparatory procedures are not possible when surgical procedures must be performed on an emergency basis.

Therefore, there is a need in the medical profession and especially, but not exclusively, in the surgical arts for an efficient, quick and effective system, including attendant methods and structure, for the formation of a fibrin product including, but not limited to, a fibrin foam matrix. As such, many of the known and recognized disadvantages with prior art technology are overcome by facilitating the formation of a fibrin foam or like fibrin component in the operating room, concurrently during the performance of a surgical procedure. Moreover, such a preferred and proposed system should not include the requirement for overly complex or overly complicated customized equipment or the application of method or procedure which is time-consuming.

More specifically, a proposed system, method and corresponding structural components should preferably facilitate the separation of a blood sample such as, but not limited to, an autologous blood sample, into at least a plasma segment and a packed cell segment and the subsequent formation of fibrin foam or like fibrin product in a single container and/or cartridge. In addition, such a proposed system may also preferably incorporate the use of a rotational drive assembly such as a substantially conventional centrifuge incorporating a rotational drive motor. In cooperation therewith, a single container/cartridge should be structured to be rotationally driven to the extent of creating centrifugation of the blood sample and a resulting separation thereof into the aforementioned plasma segment and packed cell segment, as well as a possible additional separation into a "buffy coat" segment. As recognized "buffy coat" is the fraction of an anticoagulated blood sample that contains most of the white blood cells and platelets and which is separated from plasma and the red blood cells during and subsequent to centrifugation. The buffy coat segment may be used, for example, to extract DNA from the blood of mammals as well as in other technologies.

Moreover, the single container/cartridge utilized in such a proposed and preferred invention would include a plurality of chambers cooperatively disposed and structured to independently facilitate segregation of the autologous blood sample into the at least plasma and packed cell segments. The single container/cartridge would also be capable of subsequent processing of the plasma segment, utilizing air or other preferred gas compositions and a reactant composition. The reactant composition could include a thrombin or thrombin-like enzyme plus calcium in sufficient quantities and under centrifugation to facilitate the formation of the intended and desired fibrin foam or like fibrin product. Calcium is used to inhibit the anticoagulant Citrate and activate the formation of fibrin from fibrinogen through a cleavage of the fibrinogen protein.

SUMMARY OF THE INVENTION

The present invention is directed to a system which incorporates the structural and operative features of included structural components and corresponding methods for the formation of fibrin foam or other fibrin product. As practically applied, in a single container, which preferably comprises or is in the form of a cartridge, is subjected to centrifugation. The centrifugation results in the separation of an included blood sample into at least a plasma segment and a segment (erythrocytes) that is red in color and which contains most of the red blood cells. For purposes of clarity, the mostly red blood cell segment (erythrocytes) may be referred to herein as a "packed cell" segment and is distinguished from the "plasma segment" and a "buffy coat" segment. Subsequent to separation, the plasma segment is further processed to facilitate the formation of the fibrin foam or other fibrin product. Accordingly, the fibrin foam or other fibrin product may be quickly and efficiently produced while a surgical procedure is being performed, in which the produced fibrin foam product may be used.

More specifically, a container for the formation of the fibrin foam or other fibrin product comprises a cartridge structured to be rotationally driven and includes a primary chamber disposed and structured to receive a blood sample therein. The cartridge may be removably connected to a rotational drive assembly, such as a centrifuge, or otherwise be at least partially integrated into the centrifuge or rotational drive assembly. Further, the cartridge includes at least a reaction chamber and in certain additional embodiments, the cartridge may include both a reaction chamber and a cell chamber. Upon at least an initial centrifugation, sufficient centrifugal force is exerted on or applied to the blood sample to facilitate its separation into at least the aforementioned plasma segment and a packed cell segment. In addition the centrifugation may also result in the separation of a "buffy coat" segment from both the plasma and packed cell segments, as explained in greater detail hereinafter.

Due at least in part to the development of sufficient centrifugal force the plasma segment, subsequent to separation from the remainder of the blood sample, will pass independently from the primary chamber into the reaction chamber for additional processing which facilitates the formation of the fibrin foam or other fibrin product. As also explained hereinafter, such additional processing may comprise the mixing of the separated plasma segment with a gas such as, but not limited to, air already existing in the reaction chamber. In addition, the plasma segment is concurrently mixed with a reactant composition also contained or otherwise introduced into the reaction chamber. The reactant composition is provided in sufficient quantity to facilitate coagulation concurrent to the mixing of the plasma segment with the air or other gas. Accordingly, the reactant composition may take the form of a thrombin or thrombin-like enzyme and calcium. Numerous factors are known to initiate or promote the conversion of fibrinogen to fibrin. Therefore, any one or more of a number of such factors (substances) may be included in the reactant composition if sufficient activity in the conversion reaction is present to create a fibrin matrix product having useful physical properties.

In one or more additional preferred embodiments the gas maintained or introduced into the reaction chamber may be oxygen or air with an increased concentration of oxygen, in order to facilitate healing. The resulting fibrin foam or other fibrin product may be further enhanced by the addition of other agents such as, but not limited to, growth stimulants, hormones, cellular elements, bone, liver, skin, cartilage, chondroitin, platelets or other a predetermined parts of the body with which the resulting fibrin foam product is intended for use. In addition, artificial organs may benefit from a fibrin foam matrix to add cellular support.

As set forth above, the cartridge may include a plurality of chambers including, but not limited to, the aforementioned primary chamber and reaction chamber. As such, subsequent to separation of the blood sample into at least a plasma segment and the packed cell segment and concurrent to centrifugation, the plasma segment will be forced through an appropriately structured passage into the reaction chamber for processing. Concurrently, a substantially equivalent centrifugal force will be applied to the separated packed cell segment of the blood sample. In order to avoid or at least minimize passage of a portion of the packed cell segment into the reaction chamber, it may be removed from the interior of the primary chamber to an exterior thereof. Therefore, in at least one preferred embodiment, the packed cell segment is directed from the interior of the primary chamber into the aforementioned cell chamber of the cartridge, concurrent to the passage of the plasma segment from the primary chamber into the reaction chamber.

It should be apparent that adequate centrifugation of the cartridge results in the development of sufficient centrifugal force to cause the separation of the blood sample into at least the plasma segment and the packed cell segment, as indicated. Further, the resulting centrifugal force should be sufficient to direct substantially all of the plasma segment into the reaction chamber concurrently to substantially all of the packed cell segment being directed out of the interior of the primary chamber, such as into the aforementioned cell chamber.

The possibility of at least a minimal portion of the packed cell segment being passed into said reaction chamber is recognized. Accordingly, the structural features of the cartridge, including the cooperative disposition and structuring of the primary, reaction and cell chambers are such as to minimize inadvertent or undesirable mixing of the plasma segment and packed cell segment prior to or within the reaction chamber. More specifically, in at least one preferred embodiment, the primary chamber may be substantially centrally located within the canister, to the extent that the reaction chamber and the cell chamber are disposed in outwardly, substantially laterally surrounding relation to the primary chamber. As a result of this relative disposition, the development of sufficient centrifugal force during centrifugation will facilitate the passage of the plasma segment into the reaction chamber as well as a removal of the packed cell segment from the interior of the primary chamber. Further, each of the reaction and cell chambers is disposed in independent fluid communication with the primary chamber by virtue of the provision of a plurality of corresponding passages disposed and/or extending there between. As such, the reaction chamber and the cell chamber are separated to avoid direct fluid communication there between. The absence of fluid communication between the reaction chamber and the cell chamber prohibits or at least restricts a mixing of the plasma segment and packed cell segment with one another in either of the reaction chamber and cell chamber.

Therefore, the cartridge includes at least a first passage disposed and structured to facilitate flow of the plasma segment from the primary chamber into the reaction chamber concurrent to the driven rotation and centrifugation of the cartridge. The cartridge also includes at least a second passage disposed and structured to facilitate flow of the packed cell segment from the interior of the primary chamber to an exterior of the primary chamber. In one or more embodiments of the cartridge which incorporate both the reaction chamber and a cell chamber, the packed cell segment is directed through the second passage into the interior of the cell chamber. Substantially at the same time, the plasma segment is directed or forced, by the presence of centrifugal force, through the first passage into the reaction chamber. Accordingly, the passage of the plasma segment and the packed cell segment respectively and independently into the reaction chamber and the cell chamber occurs while the cartridge is being rotationally driven to establish the intended and desired centrifugal force present during centrifugation of the cartridge.

Yet additional structural and operative features of the cartridge, which are directly associated with at least the first passage, may include at least one valve structure positionable between closed and opened orientations. The valve structure assumes a closed orientation during at least the initial centrifugation and until separation of the blood sample has separated into the plasma and packed cell segments. Subsequent to such separation the valve structure may be manually or "automatically" positioned into the open orientation, by a valve actuator. As set forth in greater detail hereinafter, the valve actuator may be manually operated or actuated based on visual observation of the separation of the blood sample within the interior of at least the primary chamber. In addition, the valve actuator may be operated/activated "automatically" by a determination of separation of the blood sample within the primary chamber. Such "automatic" actuation of the valve actuator may occur through the provision of a photo-sensor assembly or like structure, a time-based activating assembly, a speed based (RPM sensor) activating assembly, or the like. Further, the valve actuator may comprise a solenoid assembly operatively connected to accomplish the disposition of the valve structure between the open and closed orientations.

As at least one alternative embodiment, the valve structure may be connected to or incorporated within the canister in the form of a pressure relief valve. Operation thereof would be based on the development of sufficient centrifugal force to position the pressure relief valve from a biased, normally closed orientation into an open orientation. The amount of centrifugal force required to dispose the pressure relief valve in an open orientation may be greater than that to cause a separation of the blood sample into at least the plasma segment and the packed cell segment. More specifically, a first predetermined centrifugal force may be applied to the canister by centrifugation, which would be sufficient to cause a separation of the blood sample into the plasma segment and the packed cell segment. Once such separation has been determined, an additional, increased predetermined centrifugal force may be applied to the canister, by a continued centrifugation, in order to open the pressure relief valve, allowing the plasma segment to pass from the primary chamber into the reaction chamber.

As indicated, the manual or automatic operation/activation of the valve actuator, resulting in positioning of the valve structure in an open orientation, is accomplished upon a determination that the initial blood sample has in fact separated into at least the plasma segment and the packed cell segment. As further indicated, the separation of the blood sample and the passage of the plasma segment and the packed cell segment out of the primary chamber occurs during centrifugation and is based on sufficient centrifugal force being exerted on the cartridge.

Yet additional features associated with one or more preferred embodiments of the present invention is the inclusion of a mixing structure disposed at least partially within and/or contiguous the entrance to the reaction chamber. Such mixing structure may assume different sizes, configurations and locations and is disposed in at least partially interruptive relation to the flow of the plasma segment into and/or within the reaction chamber. Such interruptive engagement with the plasma segment flow results in the creation of turbulence and/or a turbulent flow of the plasma segment as it enters the reaction chamber and/or is present therein. Such turbulence will in turn result in an enhanced mixture of the air or other gas and the reactant composition within the reaction chamber.

One or more embodiments of the present invention also contemplate the utilization of a stabilizing member or structure disposed within the interior of the primary chamber so as to movably interact with the blood sample, at least initially, during centrifugation. The position and/or movement of the stabilizing member may be defined as a substantially "free movement" by not directly connecting the stabilizing member to interior portions of the primary chamber. Accordingly, moving interaction with the stabilizing member and the blood sample, during centrifugation, restricts the formation of disruptive pooling, collective grouping or other undesirable migration of the blood sample within the primary chamber, to the extent that separation thereof into the plasma and packed cell segments is not hampered. Such an undesirable collection, grouping or pooling, etc. of the blood sample within the primary chamber may be the result of vibration, initial uneven rotation of the canister or other factors. The movable interaction of the stabilizer member with the blood sample serves to substantially or at least partially evenly distribute the blood sample within the primary chamber and thereby facilitate separation thereof into at least the plasma segment and the packed cell segment.

Therefore, the system of the present invention utilizing the structural components set forth herein further comprises a method of forming a fibrin foam or other fibrin product from a plasma segment separated from a blood sample during centrifugation within a single container. Moreover, at least one preferred method of application includes the utilization of a cartridge structured to be rotationally driven and which includes at least a primary chamber and a reaction chamber, wherein a cell chamber may also be included as part of the canister. The blood sample is enclosed within the primary chamber and the cartridge and is subjected to centrifugation, through the driving rotation thereof, sufficient to separate the blood sample into at least the plasma segment and a packed cell segment. Once separated, the plasma segment is directed from the primary chamber through at least a first passage into the reaction chamber concurrent to the centrifugation of the cartridge. Substantially concurrently, the packed cell segment is directed along a second passage from the interior of the primary chamber to an exterior thereof. As such, the packed cell segment, subsequent to separation may be directed from the interior of the primary chamber into the interior of the cell chamber for collection and possible further use.

Upon passing of the plasma segment into the reaction chamber, it is mixed with a sufficient quantity of air or other appropriate gas composition and a coagulating reactant composition, concurrent to continued centrifugation resulting in the formation of the fibrin foam or other fiber product.

Additional features which may be incorporated in the present invention include the forming of the fibrin foam into a matrix or one or more different structural configurations. More specifically, it is further contemplated that the resulting fibrin foam formed in the reaction chamber may be subsequently forced there from through an apertured outer barrier, partition or wall during centrifugation. As such passage of the fibrin foam, through a plurality of apertures of predetermined size, configuration and disposition will result in the formation of a plurality of thin fibrin "threads". In turn, the collection of such threads may be blended, twisted or otherwise formed into more practically usable items such as suture material or the like. This additional feature of forming "fibrin threads" is at least minimally similar to the formation of "cotton candy" wherein spun sugar is formed in thin thread like components and collected on an exterior "catch" wall where it may be collected and shaped into a more useable form, object, etc. Therefore, it should be apparent that the advantages of the present invention, including the various preferred embodiments thereof, results in the formation of a fibrin product capable of assuming different sizes, configurations, formats, matrices, etc. thereby enhancing the utilitarian versatility the resulting fibrin foam product being formed.

Yet additional features associated with one or more preferred embodiments of the present invention is the inclusion of a mixing structure disposed at least partially within and/or contiguous the entrance to the reaction chamber. Such mixing structure may assume different sizes, configurations and locations and is disposed in at least partially interruptive relation to the flow of the plasma segment into and/or within the reaction chamber. Such interruptive engagement with the plasma segment flow results in the creation of turbulence and/or a turbulent flow of the plasma segment as it enters the reaction chamber and/or is present therein. Such turbulence will result in an enhanced mixture of the plasma segment with the air or other gas and the reactant composition within the reaction chamber.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
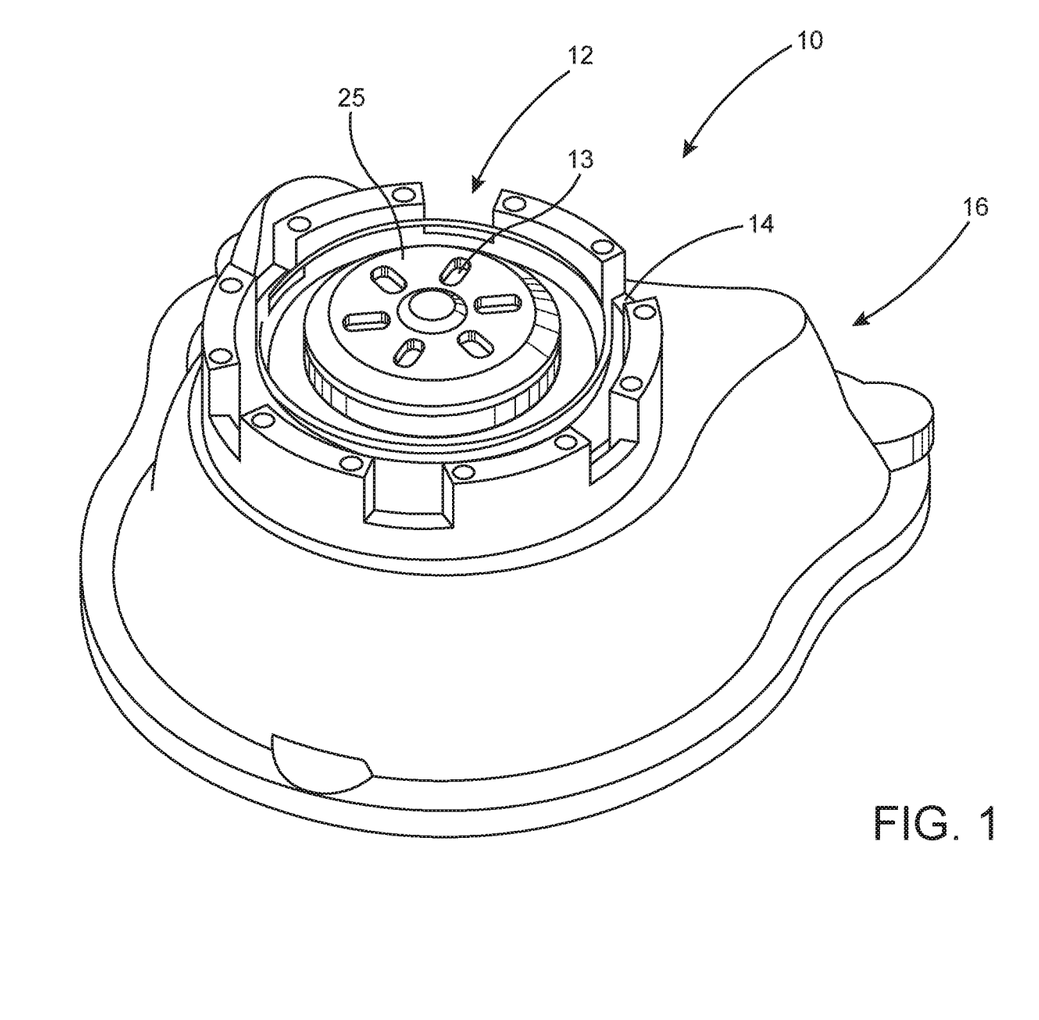
FIG. 1 is a perspective view of one embodiment of the present invention including a container connected to a centrifuge or like rotational driving assembly.

As represented in the accompanying Figures and with initial reference at least to FIGS. 1 and 2, the system of the present invention is represented by the included structure, generally indicated as 10, as well as an operatively associated method, representative of a practical application of the structure 10, as explained in greater detail hereinafter.

More specifically, the present invention includes the use of at least one container generally indicated as 12 including a canister 14. The canister 14 is structured to be rotationally driven by a rotational drive assembly 16, which may be in the form of a centrifuge structure as explained in greater detail in FIG. 2. Further, the cartridge 14 may be removably connected in driven relation to the rotational drive assembly or centrifuge 16 or may be at least partially integrated as a part thereof.

Figure 2:
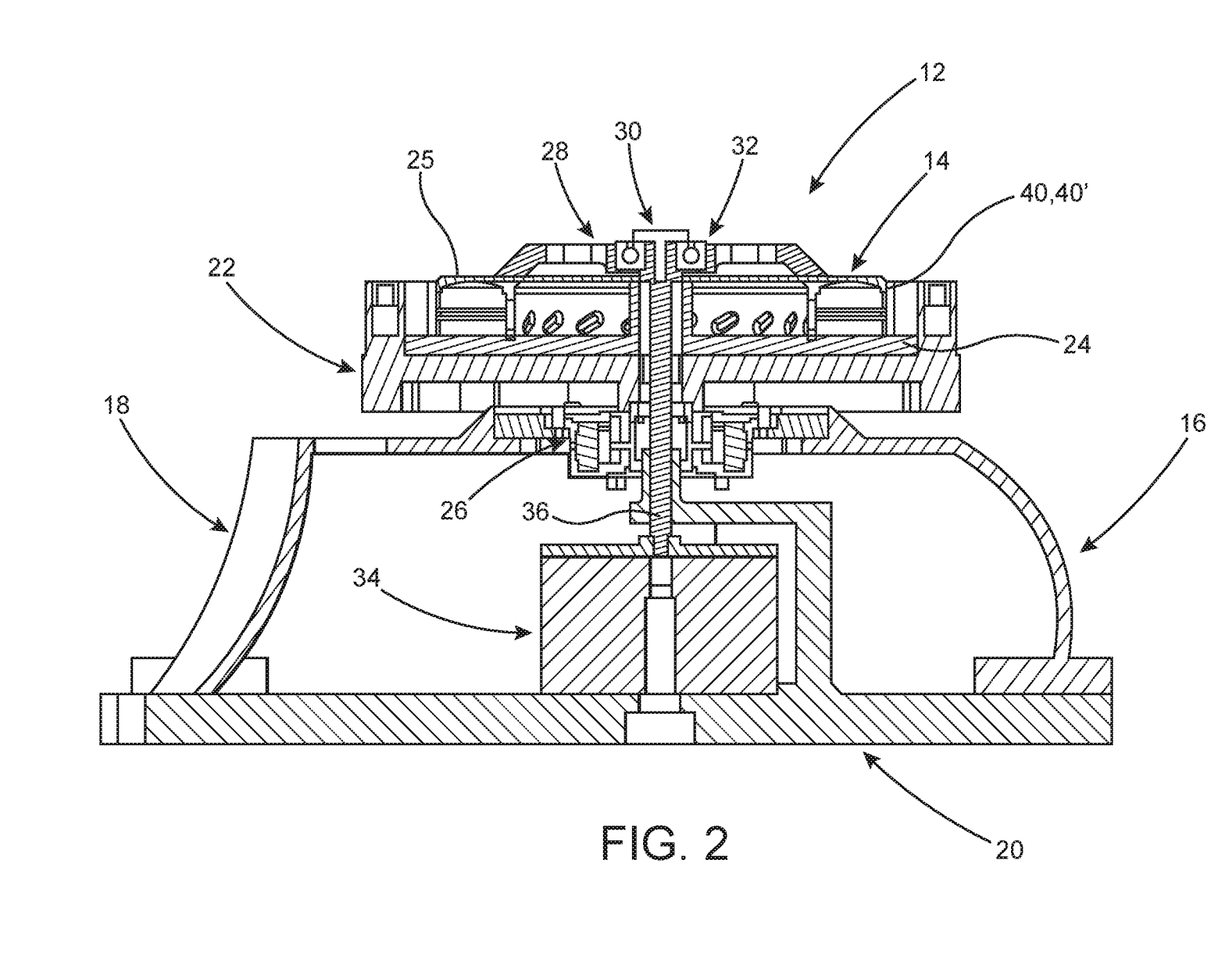
FIG. 2 is an interior, sectional view of the embodiment of FIG. 1.

As represented in FIG. 2, the rotational drive assembly or centrifuge 16 includes a housing 18 and a supporting base 20. Further, centrifuge 16 may also include a platform or "nest" 22 for support and driving interconnection with a base 24 of the canister 14. Therefore, when the canister 14 is disposed in an operative position, as represented in FIG. 2, it is drivingly connected to the rotational drive assembly or centrifuge 16 by virtue of its engagement with the nest or platform 22. In certain alternate embodiments, the nest or platform 22 may be considered a part of the canister 14 or a part of the centrifuge 16. In addition, the rotational drive assembly or centrifuge 16 includes a drive motor generally indicated as 26 appropriately mounted on the housing 18 so as to accomplish the intended driven rotation and centrifugation of the canister 14.

When operatively, but removably, connected to the centrifuge 16, the canister 14 includes a cover 25 which serves to cover an open end 40 of the canister 14 and close the interior thereof. Entry of a blood sample into the interior of the canister 14 and more specifically the primary chamber 42 may occur by passing through the opened and 40 or other inlet port or structure, dependent on the overall structural configuration of the canister 14. In addition, a closure device or "spider" cap 28 engages and effectively clamps the cover 25 down onto and in substantially sealing engagement with the outer periphery 40' of the open end 40 during centrifugation of the canister 14. Removable attachment of the cap 28 is accomplished by a connector 30, wherein a bearing assembly 32 serves to facilitate secure mounting of the cap 28 in clamping, closing relation to the cover 25 concurrent to forced rotation of the canister 14 during operation of the centrifuge 16.

In at least one preferred embodiment, a solenoid assembly 34 is provided preferably, but not necessarily, on the interior of the housing 18. The solenoid assembly 34 may be connected to the cap 28 by virtue of a shaft or spindle 36 passing through channel or opening 37 formed in the canister 14. Accordingly, upon activation of the solenoid assembly 34 the cap 28 is forced downwardly into a clamping engagement with the cover 25. Due to an at least partially flexible construction of the cover 25, a sealing engagement between the cap 25 and the periphery 40' of the open end 40 of the canister 14 will occur. In contrast, a second activation or release of the solenoid assembly 34 will at least slightly raise the cap 28, in turn resulting in a release of the sealing, clamping engagement between the cover 25 and the periphery 40' of the open end 40. As explained in greater detail hereinafter, the cap 28 and cover 25 may also be associated with a first passage 50 within the interior of the canister 14 facilitating transfer of a plasma segment, out of a primary chamber 42 within the canister 14.

Figure 3:
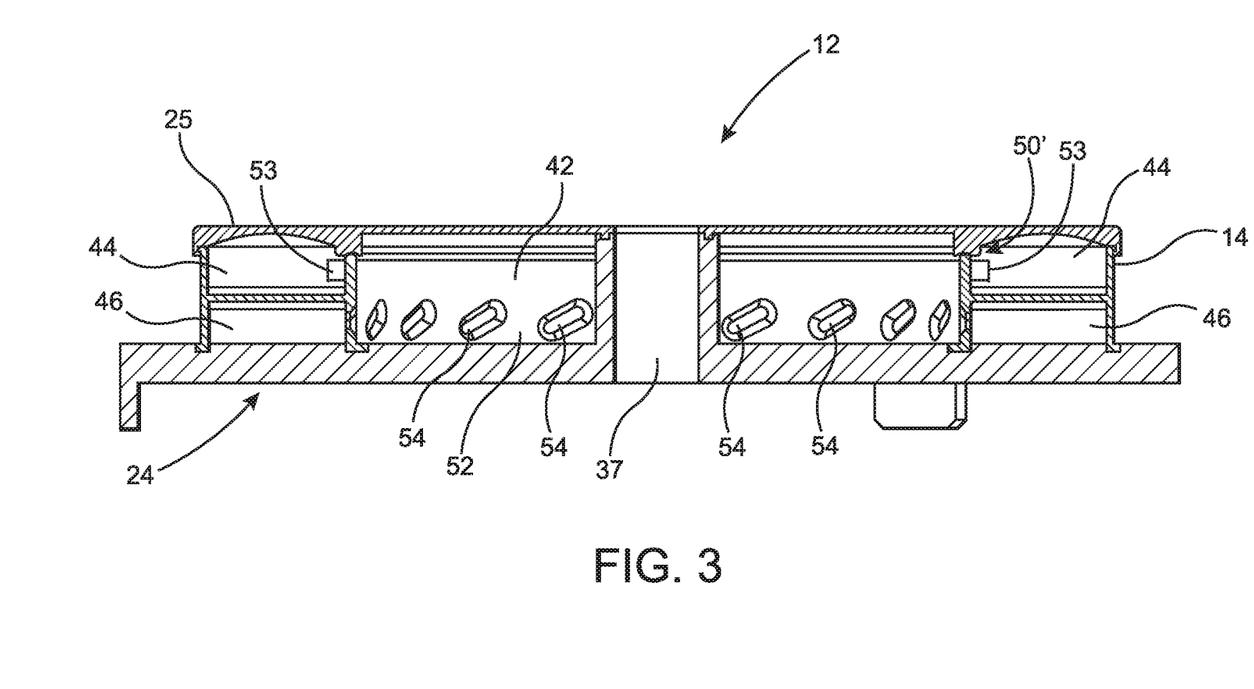
FIG. 3 is an interior sectional view of a container and canister associated with the embodiments of FIGS. 1 and 2.

Therefore, and with primary reference to at least FIGS. 2 and 3, the canister 14 of the container 12 includes the primary chamber 42 and at least a reaction chamber 44. In one or more preferred embodiments, as represented in at least FIGS. 3 and 4, the canister 14 also includes at least one cell chamber 46. As clearly represented, the primary chamber 42 is substantially centrally located within the interior of the canister 14. In cooperation therewith, the reaction chamber 44 and the cell chamber 46 are each located laterally and/or radially outward in substantially surrounding relation to the primary chamber 42 so as to take advantage of the centrifugal force developed during centrifugation of the canister 14. Moreover, during centrifugation sufficient, predetermined centrifugal force is exerted on a blood sample, placed within the primary chamber 42, to cause it to at least separate into the aforementioned plasma segment and packed cell segment.

Upon such separation of the supplied blood sample and during continued centrifugation, the plasma segment will pass from the primary chamber 42 into the reaction chamber 44 through at least a first passage 50. The first passage 50 is disposed between the upper periphery 40' of the open end 40 of the primary chamber 42 and an under surface or portion the cover 25, as at least partially explained above with primary reference to FIG. 2. Moreover, when the solenoid assembly 34 is activated to release clamping engagement with the cap 28 relative to the cover 25 the clamping sealing engagement between the cover 25 and the periphery 40' is released. This will facilitate passage of the separated plasma segment from an upper portion of the primary chamber 42, between the periphery 40' and the under portion of the cover 25 and through the first passage 50 into the interior of the reaction chamber 44, during the continued centrifugation of the canister 14 and the resulting development of subsequent centrifugal force on the contents of the canister 14.

Therefore, the opening and closing of the passage 50 as defined between corresponding portions of the cover 25 and upper, outer periphery 40' may define a valve structure 51 which either restricts or facilitates passage of the separated plasma segment from the interior of the primary chamber 42 through the first passage 50 into the interior of the reaction chamber 44. In this instance, the solenoid assembly 34 may be considered part of a valve actuator which serves to position the valve structure 51 (corresponding removably engaging portions of the cover 25 and periphery 40') between a closed orientation and an open orientation. Moreover, when the solenoid assembly 34 is activated to clamp the cap 28 downwardly onto the cover 25 the closed orientation of the valve 51 is established. In contrast, the open orientation of valve 51 is established upon an activation or release of the solenoid assembly 34 to release the cap 28 from clamping engagement with the cover 25 thereby serving to open the first passage 50 associated with the now open valve 51.

Figure 4:
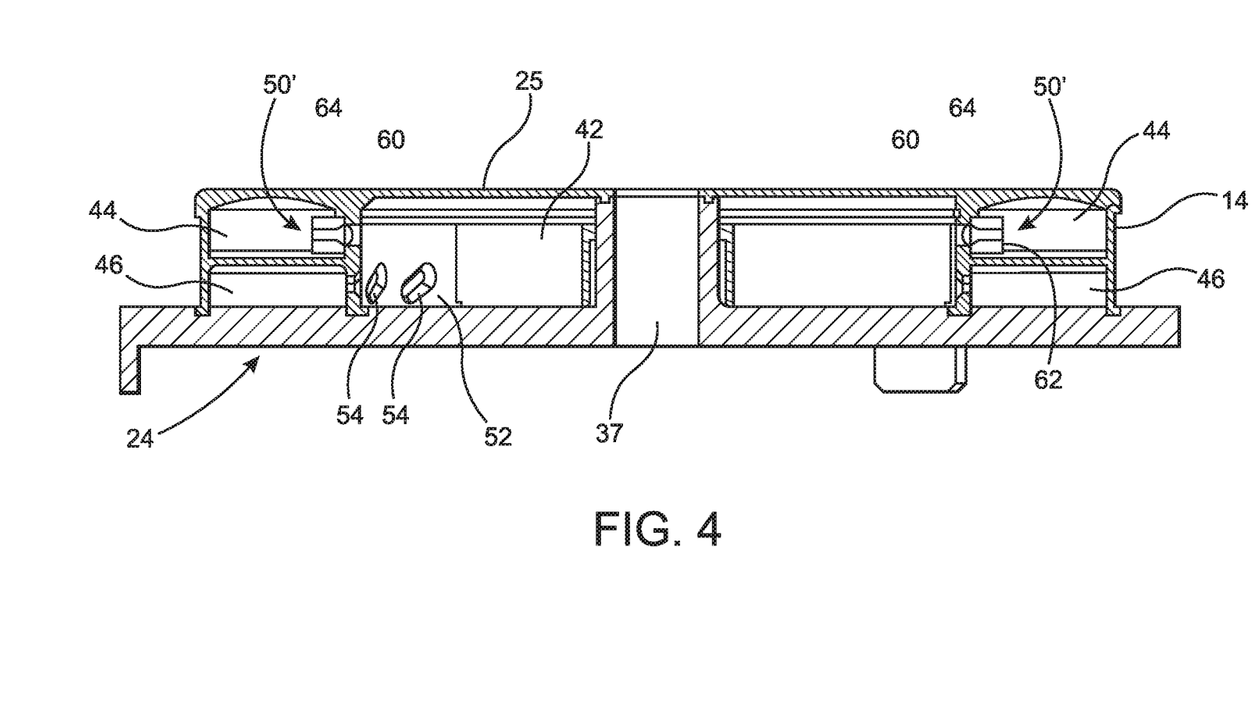
FIG. 4 is a sectional view of another embodiment of a container and canister which may be operatively associated with the embodiment of FIGS. 1 and 2.

As also represented in FIG. 3, the canister 14 includes a second passage at least partially defined by an internal barrier wall 52 disposed in surrounding relation to the primary chamber 42, and in at least partially segregating relation to the primary chamber 42 and the reaction and cell chambers 44 and 46 respectively. Further, the barrier wall 52 has an apertured construction more specifically defined by at least one but preferably a plurality of apertures 54 disposed in spaced relation to one another and collectively extending along a length of the curved barrier wall 52. It is to be noted that the one or more apertures 54 are located in a lower portion of the primary chamber 42 so as to be in substantially corresponding, fluid communicating relation to a packed cell segment of the blood sample subsequent to separation thereof from the plasma segment. The packed cell segment of the blood sample has a greater density and accordingly is "heavier" than the plasma segment. During centrifugation, the packed cell segment will therefore have a tendency to migrate towards the lower portion of the primary chamber 42 in alignment with the second passage at least partially defined by the one or more apertures 54. In the embodiment of FIGS. 3 and 4, the canister 14 is provided with a cell chamber 46. Accordingly upon centrifugation, the developed predetermined centrifugal force will direct or force the packed cell segment through the one or more apertures 54 out of the interior of the primary chamber 42. When the cell chamber 46 is present and provided within the canister 14, the outwardly directed packed cell segment will pass into the interior of the cell chamber 46 for collection and possible further use.

Yet additional features associated with one or more preferred embodiments of the present invention is the inclusion of a mixing structure 53 disposed at least partially within and/or contiguous the entrance into the reaction chamber 44. Such mixing structure(s) 53 may assume different sizes, configurations and locations and is disposed in at least partially interruptive relation to the flow of the plasma segment into and/or within the reaction chamber 44. Such interruptive engagement with the plasma segment flow results in the creation of turbulence and/or a turbulent flow of the plasma segment as it enters the reaction chamber 44 and/or is present therein. Such turbulence will in turn result in an enhanced mixture of the plasma segment with the air or other gas and the reactant composition within the reaction chamber.

Figure 5:
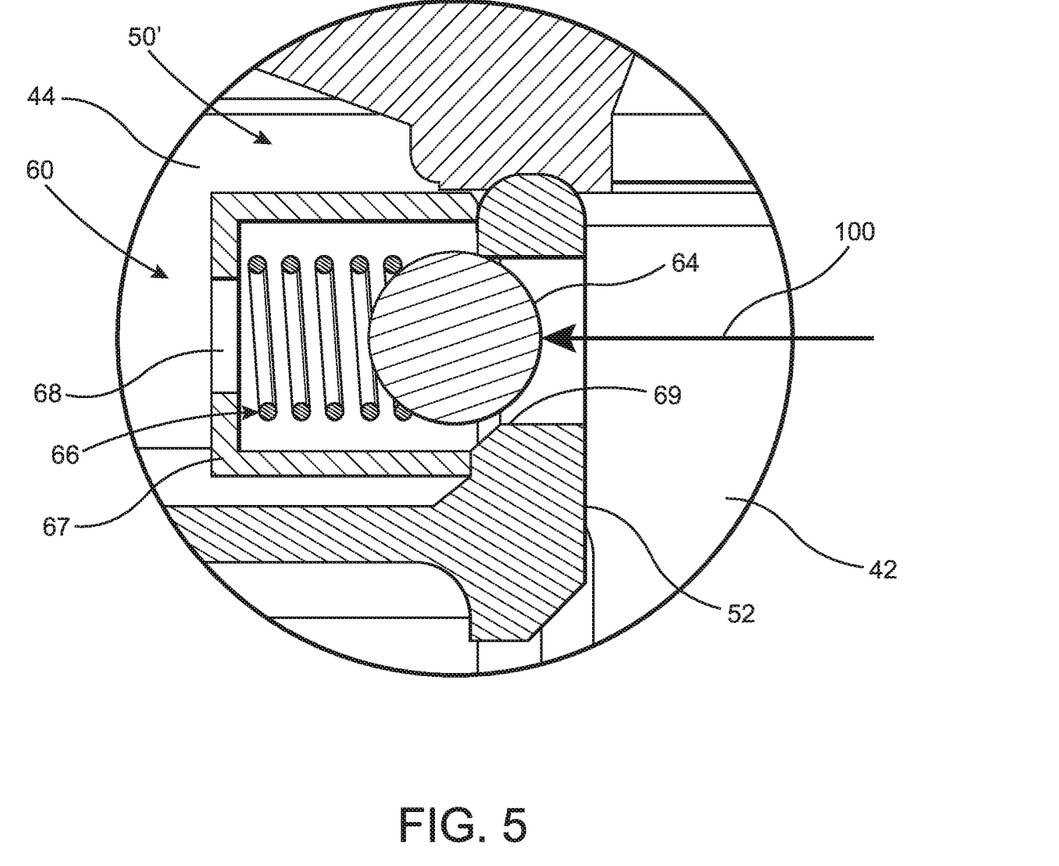
FIG. 5 is a sectional view of a pressure relief valve operatively associated with the embodiment of FIG. 4.

In yet another preferred embodiment as represented in FIGS. 4 and 5, the first passage 50 is eliminated and a different first passage 50' is substituted therefor. More specifically, the first passage 50' comprises and/or is associated with a pressure relief valve 60 including a housing 62, a biased valve member 64, and a biasing member 66 represented in detail in FIG. 5. The first passage 50' is disposed in fluid interconnecting relation between the primary chamber 42 and the interior of the reaction chamber 44. As such, the pressure relief valve 60, which at least partially defines the first passage 50', includes the valve element 64 normally biased in a closed orientation by the biasing spring or like biasing member 66. The first passage 50' is further defined by the valve housing 67 including oppositely disposed open ends 68 and 69, respectively disposed in direct fluid communication with the reaction chamber 44 and the primary chamber 42 respectively.

In use, the canister 14 is initially subjected to centrifugation to develop at least a first predetermined centrifugal force on the blood sample sufficient to cause a separation thereof into at least the aforementioned plasma segment and packed cell segment. Subsequent to separation of the blood sample, the aforementioned predetermined first or initial centrifugal force may be increased, as schematically represented by directional arrow 100, to the extent of forcing the ball valve or other valve element 64 against the biasing force of the biasing element 66 thereby opening the pressure relief valve 60 and the first passage 50'. Such opening will allow and/or direct the separated plasma segment from the primary chamber 42 through the valve housing 67 into the interior of the reaction chamber 44 during continuous centrifugation. It should be noted that while the valve element 64 is in the form of a ball, it may assume a variety of different sizes, configurations, etc. sufficient to establish a sealed engagement with the opening 69 in the barrier wall 52 and or valve housing 67.

It is emphasized that in one or more preferred embodiments the first passage 50 and/or 50' and the second passage including the one or more apertures 54 are disposed and structured to respectively establish an independent fluid communication between the primary chamber 42 and each of the reaction and cell chambers 44 and 46. Further, the reaction and cell chambers are not disposed in direct fluid communication with one another but only independently in fluid communication with the primary chamber 42.

Figure 6:
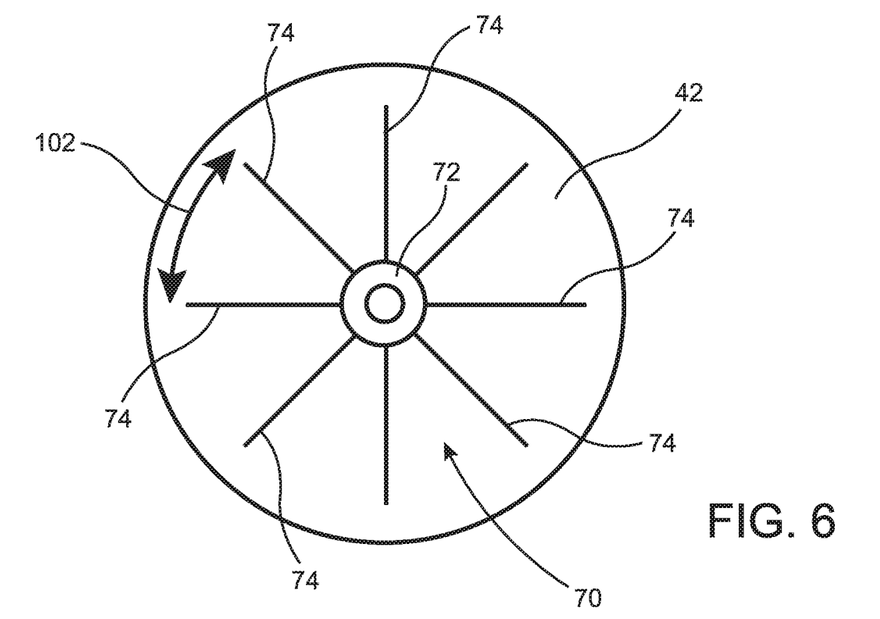
FIG. 6 is a detailed view of a stabilizing structure which may be operatively disposed within the interior of the primary chamber.
Figure 7:
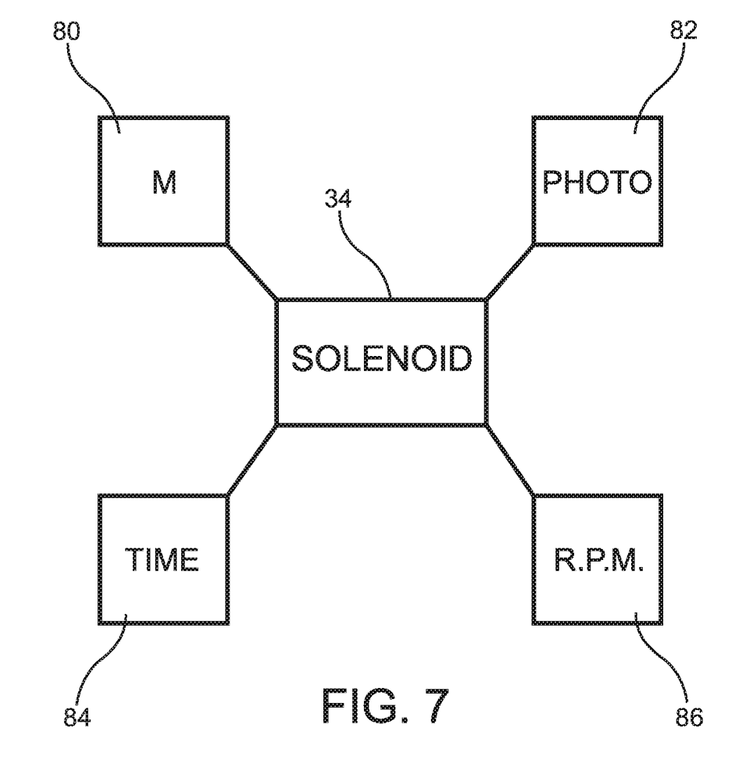
FIG. 7 is a schematic representation of a valve actuator assembly.

As represented in FIG. 6, one or more embodiments of the present invention also contemplate the utilization of a stabilizing member or structure generally indicated as 70 disposed within the interior of the primary chamber 42. When so positioned, the stabilizing member or structure 70 movably interacts with the blood sample, at least initially, during centrifugation. The position and/or movement of the stabilizing member 70, schematically represented by directional arrow 102, may be accurately described as a substantially "free movement" because it may not be directly connected to interior portions of the primary chamber 42. Accordingly, the movable interaction with the stabilizing member 70 and the blood sample, during centrifugation, prohibits or restricts undesirable migration of the blood sample and a possible formation of disruptive pooling or collective grouping of the blood sample, to the extent that separation thereof into the plasma and packed cell segments is facilitated. Such an undesirable collection, grouping or pooling, etc. of the blood sample within the primary chamber 42 may be the result of vibration, initial uneven rotation of the canister 14 or other factors. The movable interaction of the stabilizer member 70 with the blood sample serves to substantially or at least partially more evenly distribute the blood sample within the primary chamber and thereby facilitate separation thereof into at least the plasma segment and the packed cell segment. In more specific terms, the stabilizing members 70 may include a hub 72 and at least one, but preferably a plurality of outwardly, radially extending fins or vanes 74. As such, the hub 72 and the one or more vanes 74 are cooperatively dimensioned and configured to movably interact with the blood sample, within the interior of the primary chamber 42, at least during centrifugation of the canister 14.

As indicated above and with primary reference to FIG. 6, the first passage 50 may be associated with a valve structure such as the valve 51 at least partially defined by the upper peripheral portion 40' of the primary chamber 42 and corresponding engaging under portions of the cover 25. As also indicated the valve 51 may be positioned between an open orientation and a closed orientation. Such positioning of the valve 51 may be accomplished by activation and/or operation of a valve actuator which at least partially includes the solenoid assembly 34. With further reference to FIG. 6, the valve 51 may be opened by a release or corresponding activation of the solenoid assembly 34 using a manual switch or activator 80. The manual switch 80 may be activated by a visual observation of the interior of the primary chamber 42, such as through apertures 13 formed in cap 28 (see FIG. 1), thereby providing a visual indication that separation of the supply blood sample has occurred. The valve 51 and accordingly the first passage 50 may then be manually opened in order to facilitate passage of the plasma segment from the interior of the primary chamber 42, through the passage 50 and into the interior of the reaction chamber 44.

With further reference to FIG. 6, the valve actuator, at least partially including the solenoid 34, may be operated/activated "automatically" by a determination of separation of the blood sample within the primary chamber 42. Such "automatic" actuation of the valve actuator may occur through the provision of a photo-sensor assembly 82 located in operative communication with the interior of the primary chamber 42 so as to detect any change in color, light, etc. which would in turn be indicative of the separation of the blood sample at least into the plasma segment. Further, the valve actuator may also include, a time-based activating assembly 84, which detects the length of time or duration of centrifugation. It can therefore be determined that after a certain period of time of centrifugation, the developed centrifugal force is sufficient to separate the blood sample at least into the plasma segment and the packed cell segment.

In cooperation there with, a speed based (RPM sensor) activating assembly 86 may be included as part of the valve actuator. As such, when centrifuging or rotationally driving the canister 14 at a certain speed and possibly for at least a minimal duration, the blood sample will have been separated into at least the plasma and packed cell segments.

Accordingly, the manual or automatic operation/activation of the valve actuator, including the solenoid assembly 34, resulting in positioning of the valve structure 51 in an open orientation, is accomplished upon a determination that the initial blood sample has in fact segregated into at least the plasma segment and the packed cell segment. As further noted, the separation of the blood sample and the passage of the plasma segment and the packed cell segment out of the primary chamber occurs during centrifugation and is based on sufficient, predetermined centrifugal force being exerted on the cartridge 14.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A container for the formation of fibrin foam therein said container comprising:
    a cartridge structured to be rotationally driven and including a primary chamber disposed and structured for receipt of a blood sample therein,
    said cartridge further including a reaction chamber and a cell chamber disposed in segregated relation to one another and in independent fluid communication with said primary chamber,
    said reaction chamber disposed in laterally surrounding relation to said primary chamber,
    said cartridge structured to separate the blood sample into at least a plasma segment and a packed cell segment within said primary chamber under centrifugal force concurrent to a driven rotation of said cartridge,
    said reaction chamber disposed and cooperatively structured with said primary chamber to receive the plasma segment therein from said primary chamber subsequent to said separation under said centrifugal force and concurrent to said driven rotation of said cartridge,
    said reaction chamber including sufficient quantities of a gas and a reactant composition to form a fibrin foam therein under said centrifugal force, concurrent to said driven rotation of said cartridge; and
    said cell chamber disposed in fluid communication with said primary chamber and in receiving relation to the packed cell segment substantially concurrent to passage of the plasma segment into said reaction chamber and concurrent to said driven rotation of said cartridge.

2. The container as recited in claim 1 wherein said reaction chamber and said primary chamber are cooperatively disposed to receive the plasma segment in said reaction chamber independently of a majority of the packed cell segment.

3. The container as recited in claim 1 further comprising a passage disposed in fluid communicating relation between said primary and reaction chambers.

4. The container as recited in claim 3 wherein said passage includes a valve structure disposable between an open orientation and a closed orientation, said open and closed orientations respectively defining flow into and segregation of the plasma segment from said primary chamber.

5. The container as recited in claim 4 wherein said valve structure comprises at least one pressure relief valve disposable into said open orientation upon a predetermined centrifugal force exerted thereon, concurrent to said driven rotation of said cartridge.

6. The container as recited in claim 4 wherein said valve structure comprises an opening and a closure disposed between said primary and reaction chambers, said closure positioned relative to said opening from said closed orientation into said open orientation upon predetermined activation of a valve actuator.

7. The container as recited in claim 6 wherein said operation of said valve actuator comprises a manual activation thereof.

8. The container as recited in claim 7 wherein said manual activation is at least partially dependent on a visual observation of an interior of at least said primary chamber.

9. The container as recited in claim 6 wherein said predetermined operation of said valve actuator comprises a time-based actuation corresponding to a duration of said driven rotation of said cartridge.

10. The container as recited in claim 6 wherein said predetermined operation of said valve structure comprises photosensitive activation corresponding to and determinative of said separation of said plasma segment and said packed cell segment within said primary chamber.

11. The container as recited in claim 6 wherein said valve actuator further comprises a solenoid assembly.

12. The container as recited in claim 1 further comprising a mixing structure at least partially disposed in interruptive relation to flow of the plasma segment within said reaction chamber.

13. The container as recited in claim 12 wherein said mixing structure is disposed and structured to facilitate an at least partially turbulent flow of the plasma segment within said reaction chamber.

14. The container as recited in claim 1 further comprising a stabilizing structure disposed within said primary chamber and structured to facilitate a stable distribution of the blood sample within said primary chamber.

15. The container as recited in claim 1 wherein said cell chamber is disposed in laterally surrounding relation to said primary chamber; passage of the packed cell segment from said primary chamber into said cell chamber is at least partially dependent on centrifugal force resulting from driven rotation of said cartridge.

* * * * *